United States Patent [19]

Evans et al.

[11] 4,397,786
[45] Aug. 9, 1983

[54] METHOD OF PREPARING STATINE AND DERIVATIVES

[75] Inventors: Ben E. Evans; Kenneth E. Rittle, both of Lansdale, Pa.

[73] Assignee: Merck & Co., Inc., Rahway, N.J.

[21] Appl. No.: 324,207

[22] Filed: Nov. 23, 1981

[51] Int. Cl.$^3$ ............... C09F 5/00; C09F 7/00; C11C 3/00
[52] U.S. Cl. ............... 260/404; 260/410.9 R
[58] Field of Search ............... 260/404, 410.9 Q

[56] References Cited

U.S. PATENT DOCUMENTS

| | | | |
|---|---|---|---|
| 2,610,212 | 9/1952 | Floyd | 260/404 |
| 2,777,873 | 1/1957 | Hasek | 260/404 X |
| 2,956,066 | 10/1960 | Minisci | 260/404 |
| 3,288,826 | 11/1966 | Eiter | 260/410.9 Q |
| 3,544,606 | 12/1970 | Singer | 260/404 |

Primary Examiner—Helen M. S. Sneed
Attorney, Agent, or Firm—Raymond M. Speer; Hesna J. Pfeiffer

[57] ABSTRACT

Statine (Sta), a naturally-occurring amino acid and closely related derivatives, are prepared by a novel method involving an oxidative route to the requisite chiral α-aminoaldehyde intermediate, L-leucinal; the novel method may be illustrated by the following reaction scheme:

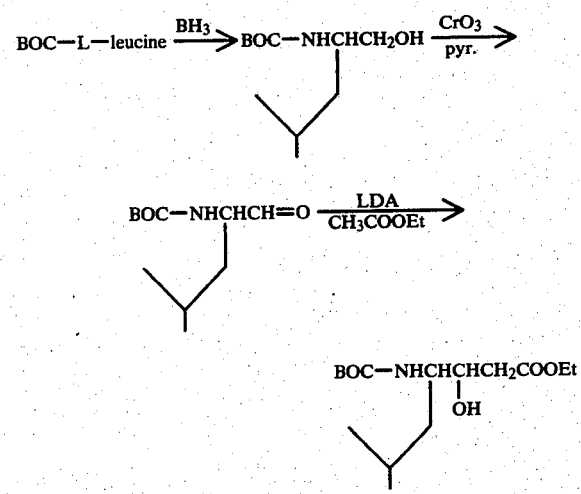

7 Claims, No Drawings

METHOD OF PREPARING STATINE AND DERIVATIVES

BACKGROUND OF THE INVENTION

1. Field of the Invention

The present invention is concerned with a novel method of preparing statine, a naturally occurring amino acid, and closely related derivatives thereof.

Statine (Sta), which may be named as 4(S)-amino-3(S)-hydroxy-6-methylheptanoic acid, is an essential component of pepstatin, a naturally-occurring low-molecular-weight peptide first isolated from actinomyces and found to be a potent inhibitor of acid proteases such as pepsin, cathepsin D, and renin. See Umezawa et al., *J. Antibiot.* (Tokyo) 23: 259–262, 1970. The natural pepstatin pentapeptide contains two statine residues, and was found by Gross et al., *Science* 175: 656, 1971, to reduce blood pressure in vivo after the injection of hog renin into nephrectomized rats. Statine is also an essential component of certain novel renin inhibitory peptides described in applications Ser. Nos. 309,854 and 309,855, both filed Oct. 8, 1981; and Ser. No. 312,528, filed Oct. 19, 1981.

2. Brief Description of the Prior Art

The method of the present invention, like those utilized in the past to prepare statine, goes through an α-aminoaldehyde intermediate. However, unlike most such prior art methods, the method of the present invention utilizes a novel oxidative route to the α-aminoaldehyde intermediate which provides good overall yield and facility of preparing the statine final product.

For example, Steulmann and Klostermeyer, in *Liebigs Ann. Chem* 1975, 2245–2250, describe synthesis of BOC-L-leucinal by reduction of tert-butyloxycarbonyl-L-leucine imidazolide with $LiAlH_4$. The ethyl ester of protected statine is then prepared by reacting the intermediate with the lithium compound of ethyl acetate. Alkaline saponification liberates the N-protected statine.

Kinoshita et al., *Bull. Soc. Chem. Japan* 48(2): 570–575 (1975), describe preparation of (−) (3S,4S) statine and its (+) (3S,4R) diastereomer starting from 3-deoxy-1,2-O-isopropylidene-α-D-erythro-pentodialdo-1,4-furanose.

Liu et al., *J. Org. Chem.* 43(4): 754 (1978) describe preparation of statine by means of a Reformatsky reaction sequence using the zinc enolate of tert-butyl acetate, starting with N-phthalyl-L-leucinal. They also describe an earlier statine synthesis reported in Morishima et al., *J. Antibiot.* 26:115 (1973). See also Liu et al., *J. Med. Chem.* 22(5): 577 (1979).

In all of the prior art methods referred to above, the protected chiral α-amino aldehyde intermediate is prepared by partial reduction of an L-leucine derivative. In fact, nearly all of the presently utilized methods for preparing chiral α-aminoaldehydes involve such a partial reduction approach. See Ito et al., *Chem. Pharm. Bull.* 23(12): 3081 (1975). See also Sharma et al., *J.C.S. Chem. Comm.* 1979: 875, who describe an exception involving periodate oxidation of diols.

One of the primary disadvantages of the prior art methods described above is the shortage of satisfactory methods for carrying out such selected reduction conveniently on a large scale and with retention of stereochemistry. For example, the most efficient method presently available for preparing statine uses a diisobutylaluminum hydride (Dibal) reduction of BOC-L-leucine ethyl ester to prepare the BOC-L-leucinal intermediate. See Rich et al., *J. Org. Chem.* 43: 3624 (1978). However, this method calls for rapid addition, followed by rapid quenching, of 1 M Dibal, carried out at low temperature. The total reaction time is reported to be 6 min. and the reaction temperature −78° C. Thus, any attempt to scale up this method could pose technical problems.

Despite the drawbacks discussed above involving aldehyde synthesis based on partial reduction of carboxylic acid derivatives, little attention has been given to preparation of chiral α-aminoaldehydes by partial oxidation of carbinols. Preparation of aldehydes generally by different methods involving partial oxidation of carbinols is described in March, "Advanced Organic Chemistry: Reactions, Mechanism, and Structure," 2 ed.; McGraw-Hill: New York, 1977; pp. 1082–84. Perhaps one reason for the failure heretofore to employ the partial oxidation route to chiral α-aminoaldehydes is the presumed tendency of the media involved to racemize the sensitive aldehyde products.

In contrast to the methods of preparing statine and other α-aminoaldehydes employed in the past, the novel method of the present invention is rapid, convenient, and amenable to large scale work. The intermediate aldehyde is produced with nearly complete retention of chiral integrity.

DETAILED DESCRIPTION OF THE INVENTION AND PREFERRED EMBODIMENTS

In accordance with the present invention there is provided a method of preparing compounds of the formula:

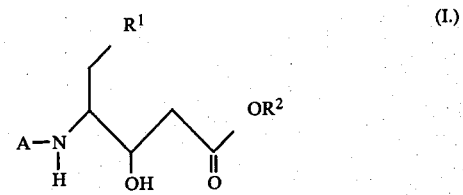

wherein:

A is hydrogen; or a blocking group B, for example tert-butyloxycarbonyl (BOC), or benzyloxycarbonyl (CBZ);

$R^1$ is $C_{3-6}$ alkyl; $C_{3-7}$ cycloalkyl; phenyl; or phenyl monosubstituted with a member selected from the group consisting of methyl, trifluoromethyl, hydroxy, methoxy, fluoro, chloro, bromo, and iodo; and $R^2$ is hydrogen; or $C_{1-4}$ alkyl;

comprising the following steps:

(a) reducing a compound of the formula:

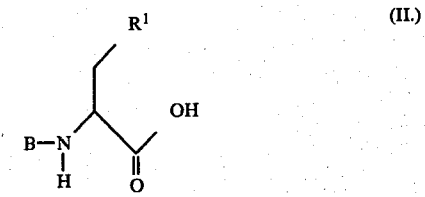

to form the corresponding carbinol of the formula:

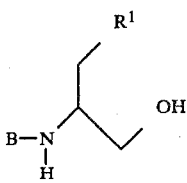

(b) oxidizing the carbinol of Formula III with chromium trioxide and pyridine in methylene chloride to form the corresponding aldehyde of the formula:

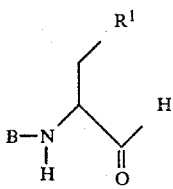

and;

(c) treating the aldehyde of Formula IV with an organometallic derivative of acetic acid or its $C_{1-4}$ alkyl ester, followed by enantiomer separation, to form a compound of Formula I of the desired chirality where A=B; and, optionally, N-deprotecting to form the Formula I compound where A is hydrogen.

These steps of the method of the present invention may be illustrated by the following reaction scheme:

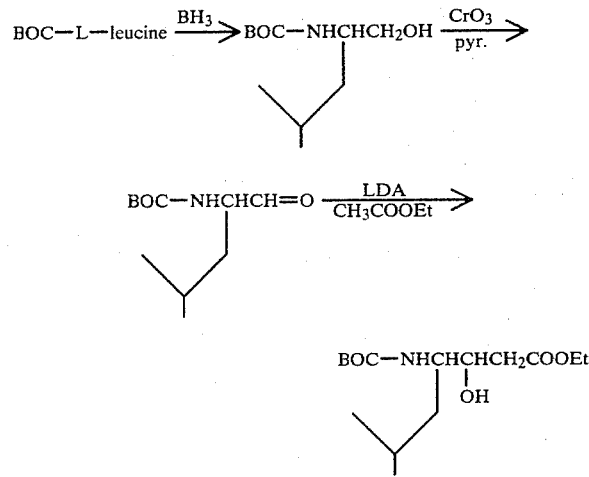

The blocking group B may be any conventional blocking group for peptide synthesis which will not interfere with the reactions carried out in the various steps of the method of the present invention. Tert-butyloxycarbonyl (BOC) and benzyloxycarbonyl (CBZ) are preferred blocking groups, while a phthaloyl blocking group should not be employed.

The organometallic derivatives of acetic acid or its $C_{1-4}$ alkyl ester are those conventionally employed in the prior art, and specifically include lithium, magnesium bromide and chloride, and zinc bromide and chloride as the metallic portion. Lithium is preferred.

The starting materials of Formula II, which are leucine or its derivatives, with a blocking group, are readily available or may be prepared using well-known methods. All of the derivatives, with the exception of the hydroxyphenyl derivatives, may be carried through the steps of the method of the present invention without any need for using conventional blocking groups. In the case of the hydroxyphenyl derivatives, such conventional blocking groups should be employed.

The method of the present invention is useful in preparing the other three stereoisomers of statine, although the primary interest is focused on the (3S,4S) stereoisomer, to which the name "statine" refers. Thus, the other stereoisomers of 4-amino-3-hydroxy-6-methylheptanoic acid: (3S,4R), (3R,4S), and (3R,4R), may also be prepared with equal accessibility and with the same retention of stereochemistry, i.e., chiral integrity, as is the case with preparation of statine itself.

The first step of the method of the present invention involves reduction of the leucine or leucine derivative starting material of Formula II to form the corresponding carbinol of Formula III. This reduction is preferably carried out using borane in an inert solvent such as tetrahydrofuran. The reaction takes place rapidly and in high yield.

In the second step, as described above, the carbinol of Formula III is oxidized to the corresponding aldehyde of Formula IV with chromium trioxide and pyridine in methylene chloride. This reaction is carried out at room temperature for about fifteen minutes and gives a good yield. This type of oxidation is described in Collins et al., *Tet. Lett.*, 1968, 3363.

The chiral stability of the α-aminoaldehydes of Formula IV was determined by taking samples immediately after the oxidation step and storing them at 0° C. and at ambient temperature, and then assaying them for chiral purity. This assay was carried out by reducing the aldehyde samples with sodium borohydride to the corresponding carbinol, followed by oxidation with permanganate to BOC-leucine. The BOC protecting group was then removed with acid, and the samples were converted to the corresponding 5-dimethylaminonaphthalene-1-sulfonyl(dansyl)derivatives by the procedure of Gros and Labouesse, *Eur. J. Biochem.* 7: 463 (1969). The chiral purities of the resulting dansyl compounds were determined by the method of Lam et al., *J. Chromatog.* 199: 295 (1980). It was found that the reduction and oxidation steps of the method of the present invention generate the aldehyde of Formula IV with complete (greater than 99.5%) retention of chiral integrity. However, it was also found that the aldehyde is chirally labile, retaining its chirality reasonably well at lower temperatures (5% racemization after 9 days at −30° C.), but racemizing relatively rapidly at room temperature (62% racemization after 9 days).

In the third step of the method of the present invention, the aldehyde of Formula IV is treated with an organometallic derivative of acetic acid or its $C_{1-4}$ alkyl ester. In a preferred procedure, the aldehyde is combined with α-lithio ethyl acetate as described in Rich et al., *J. Org. Chem.* 43: 3624 (1978). However, the silica gel chromatography separation of the 3S,4S and 3R,4S diastereomers recommended there is replaced with the flash chromatography procedure of Still et al., *J. Org. Chem.* 43: 2923 (1978), which allows processing of considerable material in a short period of time. The BOC ethyl ester obtained from this procedure has been found to be free of the 3R,4S diastereomer and its 3S,4R enantiomer, as shown by gas chromatography.

Where it is desired to obtain the final product of Formula I as an acid rather than an ester, the ester obtained with the preferred procedure described above employing α-lithio alkyl acetate may be hydrolyzed to the corresponding acid. Alternatively, the dilithio salt of acetic acid may be employed in the third step, whereby the acid form is obtained directly.

The statine and statine derivative amino acids prepared by the method of the present invention are preferably prepared with a blocking group at the N-terminus, since the amino acid would be used in this form for further peptide synthesis. Where the amino acid, per se, is preferred, it may be prepared from the corresponding N-protected compound by removal of the protecting group though conventional procedures.

Since, as described above, the aldehyde intermediate of Formula IV is chirally labile, a further aspect of the present invention provides a chiral purity assay for statine, which is described below.

Where, for example, the statine of Formula I was prepared wherein B is BOC, $R^1$ is isopropyl, and $R^2$ is ethyl, saponification gave the BOC amino acid ($[\alpha]_D^{24} = -39.5°$), which was N-deprotected to yield the free amino acid. Treatment with L-glutamic acid N-carboxyanhydride (L-Glu-NCA) according to the procedure of Manning and Moore, *J. Biol. Chem.* 243: 5591 (1968), gave a dipeptide which was shown by high performance liquid chromatography (HPLC) to contain a single major component (greater than 99.5%) of retention time (RT) 11 min, along with a minor fraction (less than 0.5%) of RT 20 min. A sample of partially racemic compound of Formula I wherein B is BOC, $R^1$ is isopropyl and $R^2$ is hydrogen, $[\alpha]_D^{24} = -30.7°$, was subjected to the same assay procedure, and showed significant amounts of both the RT=11 min (86%) and RT=20 min (14%) components. In order to verify the identity of the RT=20 min fraction, authentic 3R, 4R compound of Formula I wherein B and $R^2$ are hydrogen and $R^1$ is isopropyl (BOC amino acid $[\alpha]_D^{24} = +39.1°$) was prepared in accordance with the procedures of the present invention, using BOC-D-leucine as the starting material. The dipeptide derived from this compound and L-Glu-NCA showed the expected major component (greater than 99%) of RT=20 min by HPLC along with the minor (less than 1%) RT=11 min fraction.

The chiral purity assay described above demonstrates that the 3R,4R and 3S,4S enantiomers of the compounds of Formula I can be distinguished quantitatively; and that the compound of Formula I wherein B is BOC, $R^1$ is isopropyl, and $R^2$ is hydrogen, $[\alpha]_D^{24} = -39.5°$ is about 99.5% chirally pure 3S, 4S BOC statine.

The following examples, which have actually been carried out, will serve to further illustrate the method of the present invention without, however, constituting any limitation thereof.

EXAMPLE 1

Preparation of
3S,4S-BOC-4-amino-3-hydroxy-6-methylheptanoic acid (BOC-statine)

Step A. BOC-L-Leucinol

To a solution of BOC-L-leucine.$H_2O$ (100.0 g, 0.401 mol) in teterahydrofuran (500 ml) stirred at 0° C. under a nitrogen atmosphere, was added dropwise over a 2 h period, 1000 ml of 1 M $BH_3$ in teterahydrofuran. After addition was complete, the resultant suspension was warmed to 25° C. and stirred 1 h. With cooling, water (100 ml) was added dropwise and the solvent removed under reduced pressure. The white solid residue was slurried with water (500 ml) and extracted with ether (2×500 ml). The ethereal extracts were combined, washed with dilute aqueous $NaHCO_3$ (2×250 ml) and brine (200 ml), dried over $Na_2SO_4$ and filtered. Evaporation of the filtrate under reduced pressure gave 70.9 g (81% yield) of the title compound as a light yellow oil homogeneous to TLC ($R_f=0.40$; silica GF in 5% MeOH, 95% $CH_2Cl_2$);

$^1$H NMR ($CDCl_3$)δ0.90 (d, 6 H, $CH_3$, J=7 Hz), 1.27-1.75 (m, 3 H, —C$\underline{H}$—C$\underline{H}_2$—), 1.40 (s, 9 H, (C$\underline{H}_3$)$_3$C), 3.30-3.80 (m, 4 H, N—C$\underline{H}$—C$\underline{H}_2$—O; OH, exchanged with $D_2O$), 4.95 (br d, 1 H, NH, exchanged with $D_2O$).

Step B. BOC-L-Leucinal

To a solution of dry pyridine (218 g, 2.76 mol) in $CH_2Cl_2$ (2.86 L) stirred at 0° C. under a nitrogen atmosphere, was added chromium trioxide (138 g, 1.38 mol) portionwise while the temperature was maintained below 5° C. The deep burgundy solution was allowed to warm to 20° C., then stirred vigorously and treated with a solution of BOC-L-leucinol (50.0 g, 0.230 mol) in $CH_2Cl_2$ (200 ml) added over 5 min. After 15-20 min, the $CH_2Cl_2$ was decanted and the black tarry residue extracted with fresh $CH_2Cl_2$ (2×200 ml). The organic extracts were combined and the solvent removed as quickly as possible in vacuo without heat using a dry ice/acetone condenser. The brown oily residue was treated with ether (1250 ml) and filtered through a pad of Celite. The filtrate was concentrated in vacuo and dried under high vacuum without heat to give the title compound as a light purple oil (41.2 g): $^1$H NMR ($CDCl_3$)δ0.95 (d, 6 H, $CH_3$, J=6 Hz), 1.20-1.95 (br, m, 3 H, —C$\underline{H}$—C$\underline{H}_2$—), 1.43 (s, 9 H, ($CH_3$)$_3$), 4.23 (br s, 1 H, N—C$\underline{H}$), 5.13 (br s, 1 H, NH, exchanged with $D_2O$), 7.20-8.80 (4-8% pyridine), 9.60 (s, 1 H, CHO). This product was used without further purification.

Step C. 3R,4S and 3S,4S-BOC-4-amino-3-hydroxy-6-methylheptanoic acid ethyl ester To diisopropylamine (29.0 g, 0.287 mol) in dry tetrahydrofuran (96 ml) cooled to −20° C. under an $N_2$ atmosphere, n-butyl lithium in hexane (1.46 M, 196.5 ml, 0.287 mol) was added dropwise. The solution was stirred 15 min, the temperature lowered to −78° C., and dry ethyl acetate (25.3 g, 0.287 mol) added dropwise while maintaining the temperature below −75° C. The solution was stirred 10 min and a precooled (−78° C.) tetrahydrofuran solution (142 ml) of crude BOC-L-leucinal (41.2 g, 0.191 mol) was added while the temperature was maintained below −75° C. After 12 min, 2 N HCl (146 ml) was added while the temperature was held below −65° C. The mixture was warmed to 10° C., treated with 2 N HCl to pH 2.5, and extracted with ether (3×500 ml). The ethereal extracts were combined, washed with saturated NaCl (2×200 ml), dried over $MgSO_4$, and filtered. Evaporation of the filtrate in vacuo gave 43.1 g of a light purple oil. Chromatography of the crude oil on silica gel (2.5 kg) by the procedure of Still, Kahn, and Mitra *J. Org. Chem.* 43: 2923 (1978), eluting with 20% ethyl acetate in hexane afforded 9.7 g of BOC-statine-OEt, 3S,4S ($R_f$ 0.32, 99% by GC); rechromatography of the mixed 3R/S,4S fractions gave an additional 0.5 g. $^1$H NMR ($CDCl_3$)δ0.93 (d, 6 H, CHC$\underline{H}_3$, J=6 Hz), 1.27 (t, 3 H, $CH_2$—C$\underline{H}_3$, J=6 Hz), 1.3-1.75 (m, 3 H, C$\underline{H}_2$C$\underline{H}$), 1.44 (s, 9 H, CC$H_3$), 2.50 (m, 2 H,

3.35 (s, 1 H, OH), 3.63 (br m, 1 H, CHNH), 4.03 (br m, 1 H, CHOH), 4.18 (q, 2 H, CH$_2$CH$_3$, J=6 Hz), 4.75 (br d, 1 H, NH).

Also isolated were 9.7 g of predominantly 3R,4S (86% 3R,4S; 14% 3S,4S), 6.0 g of BOC-L-leucinol and 3.6 g of BOC leucinal.

Step D. 3S,4S-BOC-4-amino-3-hydroxy-6-methylheptanoic acid (BOC-statine)

BOC-statine-OEt, 3S,4S (1.6 g, 5.27 mmol) was dissolved in dioxane (8 ml) and diluted with water (8 ml). Monitored with a meter standardized with 1:1 dioxane/pH 10 buffer, the turbid solution was treated at room temperature with 1 N NaOH (aq) to maintain the pH of the mixture between 12.0–12.2. After 1 h, TLC (20% EtOAc/80% hexane) of the clear solution indicated the disappearance of the ester. The pH of the solution was adjusted to 6.5 with 1 N HCl and the dioxane removed in vacuo. The remaining aqueous solution was acidified to pH 2.5 with 10% citric acid and extracted with ether (3×). The combined ethereal extracts were washed with saturated NaCl, dried over MgSO$_4$, and filtered. Evaporation of the filtrate gave and oil which upon treatment with ether and dilution with hexane gave BOC-statine 3S,4S as a white solid (1.0 g, 68% yield): mp 119°–120° C., [Rich et al., *J. Org. Chem.* 43: 3624 (1978): 117°–118° C.] [α]$_D^{24}$ −39.5° (c, 0.12, CH$_3$OH); [Rich et al.: [α]$_D^{24}$ −39.6° (c, 0.31, CH$_3$OH)]; $^1$H NMR (CDCl$_3$)δ0.94 (d, 6 H, CH$_3$, J=6 Hz), 1.30–1.73 (m, 3 H, CH$_2$CH), 1.45 (s, 9 H, CCH$_3$), 2.55

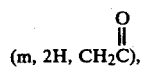

3.59 (br m, 1 H, CHNH), 4.03 (br m, 1 H, CHOH), 4.79 (br d, 1 H, NH, exchanged with D$_2$O).

Anal. Calcd for C$_{13}$H$_{25}$NO$_5$: C, 56.70; H, 9.08; N, 5.09. Found: C, 56.75; H, 9.38; N, 5.23.

EXAMPLE 2

Preparation of 3R,4R-BOC-4-amino-3-hydroxy-6-methylheptanoic acid

The procedures described above in Example 1 were repeated, but using BOC-D-leucine.H$_2$O in place of the BOC-L-leucine.H$_2$O. The product obtained had physical properties identical to those described above for the product in Example 1, Step D., except: [α]$_D^{24}$ +39.1° (C, 0.12, CH$_3$OH).

EXAMPLE 3

Chiral Stability Studies of BOC-Leucinal

Samples of BOC-leucinal prepared as described above in Example 1, Step B, were stored at room temperature and at −30° C. for periods of 0 hrs, 24 hrs, and 9 days. The samples were assayed for chiral purity as described below.

To a solution of BOC-leucinal (168 mg, 0.780 mmol) in methanol (2 ml) cooled to 0° C., was added sodium borohydride (30 mg, 0.780 mmol). After stirring 15 min, the reaction was complete by TLC. The methanol was removed in vacuo and the resulting residue slurried with water and extracted with ether (3×). The combined ethereal extracts were washed with saturated NaCl (aq) (2×), dried over MgSO$_4$, and filtered. The filtrate was stripped to dryness in vacuo to give 130 mg of BOC-leucinol as a colorless oil with properties identical to those described above in Example 1, Step A.

BOC-leucinol (130 mg, 0.598 mmol) was treated with 3.1 ml of 0.25 N NaOH followed by KMnO$_4$ (125 mg, 0.796 mmol) at room temperature and stirred 15 min. The reaction was treated with methanol, stirred 15 min, and the brown precipitate removed by filtration through Celite. The filtrate was acidified with solid citric acid and extracted with ether (3×). The combined ethereal extracts were washed with saturated NaCl (aq) (2×), dried over MgSO$_4$ and filtered. Evaporation of the filtrate in vacuo gave 130 mg of BOC-leucine as an oil homogeneous by TLC (R$_f$, 0.34; silica GF in 5% MeOH/95% CH$_2$Cl$_2$).

This material (130 mg, 0.562 mmol) was dissolved in ethyl acetate (2 ml). The solution was cooled to 0° C., saturated with HCl (g) and stirred 15 min. Evaporation of the solvent in vacuo gave an oil which was repeatedly evaporated in vacuo with ethyl acetate until a white solid precipitated. Filtration gave leucine-HCl (75 mg) which was dried in vacuo at room temperature. This hydrochloride (10 μg, 0.06 μmol) in 100 μl of 0.2 M sodium bicarbonate buffer, pH 9.0, was treated with 100 μl of a 0.02 M solution of 5-dimethylaminonaphthalene-1-sulfonyl chloride in acetone. The mixture was stirred at 37° C. for 30 min and quenched with 0.1 ml of formic acid. The mixture was evaporated to dryness under a stream of nitrogen and the residue dissolved in methanol (0.5 ml). The solution (10 μl) was analyzed by HPLC using as the mobile phase a solution of arginine (5 mM), copper sulfate.5H$_2$O (2.5 mM) and ammonium acetate (5 mM) in glass distilled water, adjusted to pH 7.8 with NH$_4$OH. Fluorescence at 520 nm was monitored with excitation at 340 nm. Samples were run in duplicate, and authentic samples of D- and L-leucine were used as controls. The observed L- to D-ratios along with measured optical rotations of the leucine HCl samples are summarized below.

| Storage time (day) | Storage temp. (°C.) | [α]$_D^{24}$ | L-/D- (HPLC) |
| --- | --- | --- | --- |
| 0 | — | +18.2° | 100/0 |
| 1 | −30 | +17.9° | 99/1 |
| 9 | −30 | +17.4° | 99/1 |
| 9 | 24 | +6.9° | 70/30 |

EXAMPLE 4

Chiral Integrity Studies of BOC-4-Amino-3-Hydroxy-6-Methylheptanoic Acid

Step A. N-Deprotection

BOC-4-amino-3-hydroxy-6-methylheptanoic acid (400 mg, 1.45 mmol) was dissolved in ethyl acetate (3 ml) and cooled to 0° C. The solution was saturated with HCl (g), stirred 15 min, then saturated with nitrogen for 15 min. Evaporation of the solvent in vacuo gave an oil which was repeatedly treated with ethyl acetate and evaporated in vacuo. The residue was dried at room temperature under high vacuum for 16 h to give the free amino acid hydrochloride as a sticky solid.

Step B. Derivatization and Separation

The compound from Step A above (20 μmol) was dissolved in pH 10 borate buffer (2 ml) and cooled to 0° C. L-Glutamic acid N-carboxy anhydride was added, and the solution was vortexed for 2 min, then quenched with 1 N HCl (1 ml). The derivatized samples were assayed by HPLC using a gradient of phosphate buffer (8.7 mM phosphoric acid adjusted to pH 3.2 with 25% aqueous trimethylamine) with acetonitrile (100/0→90/10 over 30 min) on a Waters Associates C-18 column (30×0.39 cm). The sample derived from 3S,4S showed a single major component (retention time 11 min) as did that derived from the 3R,4R material (retention time 20 min). Mixtures of weighed quantities of 3R,4R and 3S,4S were assayed by the same procedure. All the results are summarized below.

| SS/RR by weight* | SS/RR by HPLC |
|---|---|
| 3S,4S | 99.6/0.4 |
| 95.1/4.9 | 95.5/4.5 |
| 96.7/3.3 | 97.7/2.3 |
| 84.3/15.7 | 84.7/15.3 |
| 49.4/50.6 | 54.6/45.4 |
| 3R,4R | 2.3/97.7 |

*Weighed samples of 3R,4R and 3S,4S corrected for the observed contamination of each with the other.

In the above examples, the following analytical techniques and equipment were used.

Melting points were determined using a Thomas Hoover melting point apparatus and are uncorrected. $^1$H NMR spectra were obtained on a Varian T-60 or EM 390 spectrometer using $(CH_3)_4Si$ as an internal standard. Optical rotations were measured at the sodium D line using a Perkin-Elmer 241 polarimeter Gas chromatography was carried out on a Hewlett-Packard model 5710A gas chromatograph using glass columns (4 ft×4 mm) packed with 1% OV-255 on Chromosorb Q (110–120 mesh) at 165° C. The injection temperature was 255° C. HPLC assays were run on a Spectra-Physics SP8000 High Performance Liquid Chromatograph using a 25×0.4 cm analytical column packed with Dupont C-8 resin. Analytical TLC was carried out on 250 μm, 2.5×10 cm, silica gel GF plates (Analtech, Inc.) using ninhydrin spray and $I_2$ for visualization.

What is claimed is:

1. A method of preparing compounds of the formula:

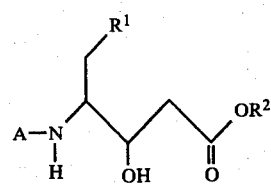

wherein
A is hydrogen; or a blocking group B conventionally employed in peptide synthesis;
$R^1$ is $C_{3-6}$ alkyl; $C_{3-7}$ cycloalkyl; phenyl; or phenyl monosubstituted with a member selected from the group consisting of methyl, trifluoromethyl, hydroxy, methoxy, fluoro, chloro, bromo, and iodo; and
$R^2$ is hydrogen; or $C_{1-4}$ alkyl;
comprising the following steps:
(a) reducing a compound of the formula:

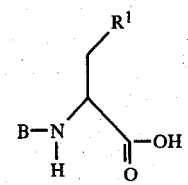

to form the corresponding carbinol of the formula:

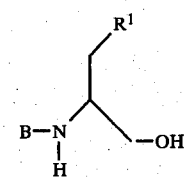

(b) oxidizing the carbinol of Formula III with chromium trioxide and pyridine in methylene chloride to form the corresponding aldehyde of the formula:

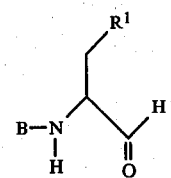

and;
(c) treating the aldehyde of Formula IV with an organometallic derivative of acetic acid or its $C_{1-4}$ alkyl ester, followed by enantiomer separation, to form a compound of Formula I of the desired chirality where A=B; and, optionally, N-deprotecting to form the Formula I compound where A is hydrogen.

2. A method according to claim 1 wherein B is tert-butyloxycarbonyl (BOC), $R^1$ is isopropyl, and $R^2$ is hydrogen.

3. A method according to claim 1 wherein the compound prepared is 3S,4S-BOC-4-amino-3-hydroxy-6-methylheptanoic acid (BOC-statine).

4. A method according to claim 1 wherein the reduction in Step (a) is carried out using borane in tetrahydrofuran.

5. A method according to claim 1 wherein in Step (c) the metallic portion of the organometallic derivative of acetic acid or its $C_{1-4}$ alkyl ester is selected from the group consisting of lithium, magnesium bromide, magnesium chloride, zinc bromide, and zinc chloride.

6. A method according to claim 5 wherein in Step (c) α-lithio ethyl acetate is used to treat the aldehyde of Formula IV.

7. A method according to claim 1 wherein in Step (c) the enantiomers are separated by flash chromatography.